United States Patent
Welzig et al.

(10) Patent No.: US 10,064,961 B2
(45) Date of Patent: Sep. 4, 2018

(54) METHOD FOR PRODUCING A LIQUID PHARMACEUTICAL PREPARATION

(71) Applicant: SANOCHEMIA PHARMAZEUTIKA AG, Wien (AT)

(72) Inventors: Stefan Welzig, Wien (AT); Raffael Schuecker, Wien (AT); Beate Kaelz, Steinbrunn (AT); Jozsef Gungl, Agfalva (HU); Klaus Gerdes, Duesseldorf (DE); Roswitha Braunrath, Marz (AT)

(73) Assignee: SANOCHEMIA PHARMAZEUTIKA AG, Vienna (AT)

( * ) Notice: Subject to any disclaimer, the term of this patent is extended or adjusted under 35 U.S.C. 154(b) by 0 days.

(21) Appl. No.: 15/500,685

(22) PCT Filed: Jun. 15, 2015

(86) PCT No.: PCT/AT2015/000088
§ 371 (c)(1),
(2) Date: Jan. 31, 2017

(87) PCT Pub. No.: WO2016/015066
PCT Pub. Date: Feb. 4, 2016

(65) Prior Publication Data
US 2017/0216462 A1    Aug. 3, 2017

(30) Foreign Application Priority Data
Jul. 31, 2014  (AT) ........................ 608/2014

(51) Int. Cl.
*A61K 9/00* (2006.01)
*A61K 49/10* (2006.01)
*A61K 9/08* (2006.01)

(52) U.S. Cl.
CPC .............. *A61K 49/108* (2013.01); *A61K 9/08* (2013.01)

(58) Field of Classification Search
CPC .................................................. A61K 49/108
See application file for complete search history.

(56) References Cited

U.S. PATENT DOCUMENTS

| 4,877,600 | A | 10/1989 | Bonnemain et al. |
| 5,560,903 | A | 10/1996 | Gries et al. |
| 2012/0082624 | A1 | 4/2012 | Port |

FOREIGN PATENT DOCUMENTS

| EP | 0 263 861 A1 | 4/1988 |
| EP | 2 242 515 B1 | 4/2014 |

(Continued)

OTHER PUBLICATIONS

Meglumine (http://jpdb.nihs.go.jp/jp14e/14data/Part-II/Meglumine.pdf: downloaded on Sep. 18, 2017).*

(Continued)

*Primary Examiner* — Paul W Dickinson
(74) *Attorney, Agent, or Firm* — Young & Thompson

(57) ABSTRACT

A method for producing a liquid pharmaceutical preparation which contains a complex consisting of DOTA and gadolinium and a base such as L-lysine or meglumine, includes the following steps: a) An aqueous solution containing free DOTA, free gadolinium and a base such as L-lysine or meglumine is produced. b) The yield of free DOTA and free gadolinium is determined in the solution obtained according to step a). c) Free gadolinium and/or free DOTA is added in order to adjust a stoichiometric excess of free DOTA in the solution. d) The complexation is executed at an increased temperature. e) Additional base such as L-lysine or meglumine is added in order to adjust the pH value. f) The final volume of the preparation is adjusted.

20 Claims, 1 Drawing Sheet

(56) References Cited

FOREIGN PATENT DOCUMENTS

| WO | 87/06229 A1 | 10/1987 | |
|---|---|---|---|
| WO | WO 2009103744 A2 * | 8/2009 | ........... A61K 49/106 |

OTHER PUBLICATIONS

International Search Report, dated Sep. 23, 2015, from corresponding PCT Application.
Austrian Search Report, dated Mar. 10, 2015, from corresponding Austrian Application.

* cited by examiner

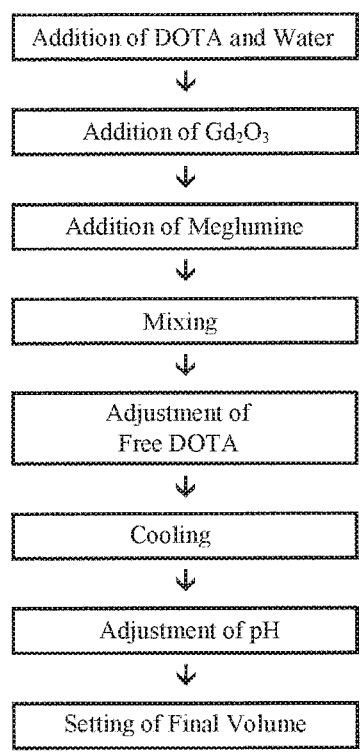

METHOD FOR PRODUCING A LIQUID PHARMACEUTICAL PREPARATION

The invention relates to a method for producing a liquid pharmaceutical preparation, which contains a complex that consists of the macrocyclic chelate DOTA (1,4,7,10-tetraazacyclododecane-1,4,7,10-tetracetic acid) with gadolinium and in addition L-lysine or meglumine as a base.

The preparation that can be produced according to the invention can be used as a contrast medium.

A method of the generic type, which is used, for example, for the production of gadoteric acid-meglumine salt, is known from EP 2 242 515 B1.

The method, known from EP 2 242 515 B 1, for producing a liquid pharmaceutical formulation, which contains a complex of macrocyclic chelate with a lanthanide, comprises the following steps:

Production of a liquid pharmaceutical composition, which contains the complex of macrocyclic chelate with a lanthanide and free macrocyclic chelate, which is not present in the form of an adjuvant X[X', L], whereby L is the macrocyclic chelate and X and X' are a metal ion, and free lanthanide, by mixing a solution of free macrocyclic chelate and free lanthanide in order to achieve complexing of the lanthanide by the macrocyclic chelate, whereby the amounts of free macrocyclic chelate and free lanthanide are such that the entire lanthanide is not complexed;

Measuring the concentration of free lanthanide in the thus obtained pharmaceutical formulation, whereby the concentration of the free macrocyclic chelate is equal to 0;

Adjusting the concentrations of free chelate and free lanthanide by adding to the thus obtained formulation the amount of free macrocyclic chelate that is necessary first of all to complete the complexing of the free lanthanide in order to ensure that there is no free lanthanide, and secondly to achieve the target concentration of the free macrocyclic chelate in the finished liquid pharmaceutical formulation, whereby the amount of free macrocyclic chelate in the finished liquid pharmaceutical formulation corresponds to the proportion of free macrocyclic chelate in relation to the amount of complexed macrocyclic chelate in the finished liquid pharmaceutical formulation.

The method that is known from EP 2 242 515 B 1 is comparatively expensive and not readily applicable on the industrial scale, since numerous adjustment steps are necessary.

A reworking of the method described in Example 2 of EP 2 242 515 B1 does not yield, moreover, any product described in EP 2 242 515 B 1, since the complexing is only around 88% complete in the case of strict adherence to the method steps of Example 2. The remaining gadolinium and DOTA thus remain uncomplexed, and the specification of $C_{ch\ 1}$ equal to 0 (concentration of free macrocyclic chelate equal to zero), mentioned in claim 1 under 1c, is not achieved. In this regard, see the comparison example.

Since the complexing components are present in complexed and free form, an adjustment of excess chelate, as indicated in Item 1d of Claim 1 of EP 2 242 515 B1, is not possible.

The object of the invention is to make available a method of the above-mentioned type, which is simpler to carry out and results in the desired pharmaceutical preparation, for example gadoteric acid-meglumine salt.

According to the invention, the object is achieved with a method of the above-mentioned type, which comprises the following steps:
a) Production of an aqueous solution that contains free DOTA, free gadolinium, and L-lysine or meglumine as a base.
b) Determination of the contents of the solution of free DOTA and free gadolinium obtained according to step a).
c) Adding free gadolinium or free DOTA in order to adjust a stoichiometric excess of free DOTA in the solution, whereby the addition of free DOTA and free gadolinium is carried out in such a way that no free gadolinium is present in the preparation,
d) Carrying out the complexing at elevated temperature.
e) Adding another base in order to adjust the pH.
f) Setting the final volume of the preparation.

It is evident that because of the special guiding of the method, the method according to the invention is simple to carry out and results, surprisingly enough, in a preparation that can be used as a contrast medium without the danger existing that free gadolinium is contained in the contrast medium. One feature of the method according to the invention is the reaction of DOTA with gadolinium in the presence of a base. In the invention, before the first measuring of the content of free DOTA and free gadolinium, the three components DOTA, gadolinium, and L-lysine or meglumine (in the reactor) are reacted together. Only the presence of a base ensures a medium is obtained that completes the complexing reaction and results in complete complexing of complexing components (gadolinium) contained in a minimal amount, so that the content of free gadolinium is equal to zero. By measuring the excess of free DOTA, gadolinium can be added in such a way that the content of free DOTA can be adjusted to a range of 200-1500 ppm, relative to the complex.

In one embodiment of the method according to the invention, it is possible to proceed in such a way that for producing the solution according to step a), first DOTA is dissolved in water at elevated temperature, and then gadolinium is added.

In one embodiment of the method according to the invention, it is possible to proceed in such a way that the adding of free DOTA and free gadolinium is carried out in such a way that no free gadolinium is present in the preparation.

In one embodiment of the method according to the invention, it is possible to proceed in such a way that the complexing is completed by further addition of a base such as L-lysine or meglumine.

In one embodiment of the method according to the invention, it is possible to proceed in such a way that step a) is carried out at a temperature of between 60° C. and 95° C.

In one embodiment of the method according to the invention, it is possible to proceed in such a way that the solution is stirred when step a) and/or d) is/are carried out.

In one embodiment of the method according to the invention, it is possible to proceed in such a way that meglumine or L-lysine is used as a base.

In one embodiment of the method according to the invention, it is possible to proceed in such a way that in step c), the addition of gadolinium is carried out in two or more than two partial amounts.

In one embodiment of the method according to the invention, it is possible to proceed in such a way that free DOTA is added in the form of a solution and/or free gadolinium is added in the form of a solution.

In one embodiment of the method according to the invention, it is possible to proceed in such a way that the gadolinium is added as oxide ($Gd_2O_3$). In this case, gadolinium is present as a trivalent cation.

In one embodiment of the method according to the invention, it is possible to proceed in such a way that the concentration of free DOTA in the preparation is 180-2000 ppm, preferably 200 to 1500 ppm.

In one embodiment of the method according to the invention, it is possible to proceed in such a way that the concentration of free gadolinium in the preparation is less than 10 ppm.

In one embodiment of the method according to the invention, it is possible to proceed in such a way that the pH in step e), in particular at room temperature, is adjusted to a value of between 7.0 and 7.2.

In the figure, the basic course of the procedure of the method according to the invention is reproduced.

When the method according to the invention for producing a liquid pharmaceutical preparation is carried out by complexing DOTA with gadolinium, for example, the following steps can be carried out:

DOTA is dissolved at an elevated temperature in water for injection purposes.

In another step, a precalculated amount of gadolinium is added, whereby it is taken into account that the calculated amount of gadolinium has to be substoichiometric, i.e., DOTA is present in stoichiometric excess.

The complexing is carried out at high temperatures over a period that is sufficient to form a complex from the gadolinium and DOTA.

The reaction of substances (DOTA and gadolinium) is completed by adding a base that is necessary for this purpose (for example, meglumine or L-lysine).

Subsequently, the concentration of free DOTA and free gadolinium is determined in order to ensure that a substoichiometric amount of gadolinium and a higher concentration of DOTA are present.

By further adjustment of the concentrations of the above-mentioned free portions (gadolinium and DOTA), the concentration is controlled in such a way that the concentration of free gadolinium in the finished preparation is equal to zero, and the concentration of free DOTA is between 200 and 1500 ppm, relative to the complex.

The forming of the complex can be carried out at a temperature in the range of between 60° C. and 95° C.

The reaction times for forming the complex depend on the course of the procedure. For example, it is stirred for two hours and then allowed to stand for ten hours.

The adjustment of the content of free DOTA and the content of free gadolinium can be performed not only using solid substances but rather also using previously produced solutions of the two substances.

Below, the comparison example, in which the method of operation of Example 2 of EP 2 242 515 B1 was applied, is reproduced.

The batch from Example 2 of EP 2 242 515 B1 was reduced by the factor 500, which corresponds to a laboratory batch size of 200 ml of total volume.

The ratio of weighed-in portions of raw materials was not changed.

After mixing DOTA and gadolinium oxide in water at 80° C., a solution was obtained. Within 48 hours, several samples were drawn, and the contents of free DOTA and complex were determined. It turned out that, on the one hand, at no time was the content of the complex greater than 88%, and, on the other hand, correlating with this, the content of free DOTA was less than 11% (see Table 1). An excess of gadolinium oxide results from the batch calculation, and thus in the case of complete complexing, a content of free DOTA that is equal to zero would be expected. Since, however, a significant proportion of uncomplexed DOTA was present in the batch, the complexing was not complete. An adjustment of the free DOTA was therefore not possible at this time, as described in EP 2 242 515 B1, Example 2, Step 3. Only by adding meglumine was a medium produced, which medium completed the complexing and significantly increased the content of the complex (see Table 1).

It is much more important, however, that in general only after adding meglumine is an adjustment of content of free DOTA possible within the desired limits, since because of the addition of meglumine, the free DOTA already in solution is completely complexed (free DOTA<50 ppm).

The results of this comparison example thus contradict the teaching of EP 2 242 515 B1.

TABLE 1

Measured Values of the Comparison Example.

| Reaction Time After Mixing DOTA and Gadolinium Oxide | Content of Free DOTA | Content of Complex |
|---|---|---|
| 1 hour | 11.4% | |
| 2 hours | 11.4% | |
| 3 hours | 11.4% | |
| 4 hours | 11.5% | |
| 8 hours | 11.9% | |
| 24 hours | 12.5% | 234 mg/ml |
| 31 hours | 13.6% | 230 mg/ml |
| 48 hours | 15.8% | 229 mg/ml |
| 48 hours; after adding meglumine | <50 ppm | 262 mg/ml |

The method that is developed according to the invention solves this problem by meglumine being added to the reaction batch as early as before the first determination of content of the free DOTA and complex. A stoichiometric excess of DOTA is used, thus ensuring a complete reaction of gadolinium to form the complex, and the content of free gadolinium in the first determination of content is equal to zero. Based on the measured values from Table 2, it can be clearly seen that only the addition of meglumine creates a medium that completes the complexing. An adjustment of content of free DOTA by adding gadolinium is then easily possible (see Table 2).

TABLE 2

Measured Values of the Method According to the Invention.

| Method Step | Content of Free DOTA | Content of the Complex |
|---|---|---|
| Mixing DOTA and gadolinium oxide | 12.7% | 252 mg/ml |
| 30 minutes after adding meglumine | 2.1% | 283 mg/ml |
| 60 minutes after adding meglumine | 1.7% | |
| 90 minutes after adding meglumine | 0.15% | |
| 60 minutes after adding gadolinium | 0.11% | |
| 90 minutes after adding gadolinium | 0.10% | 280 mg/ml |
| Setting of the final volume | 994 ppm | 278 mg/ml |
| End of the production, after 18 hours | 981 ppm | 278 mg/ml |

Below, embodiments of the method according to the invention are reproduced.

EXAMPLE 1

40.5 g of DOTA was suspended in 150 ml of water at a temperature of 75° C. 17.8 g of gadolinium oxide was added, and the batch was stirred at 75° C. for 2 hours. The solution that was produced was mixed with 19.5 g of meglumine and stirred at 75° C. for one hour. Then, the content of free DOTA, free gadolinium, and complex was determined, and the final content of excess free DOTA was set. The concentration of free gadolinium was equal to zero, and the concentration of excess free DOTA was adjusted to a value of between 200 and 1500 ppm, relative to the complex. The reaction batch was made up to a total volume of 200 ml and filtered.

EXAMPLE 2

7.8 g of gadolinium oxide was suspended in 150 ml of water at a temperature of 75° C. 40.5 g of DOTA was added, and the batch was stirred at 75° C. for 2 hours. Another 10.0 g of gadolinium oxide was added and again stirred at 75° C. for 15 minutes. The solution that was produced was mixed with 19.5 g of meglumine and stirred at 75° C. for one hour. Then, the content of free DOTA, free gadolinium, and complex was determined, and the final content of excess free DOTA was set. The concentration of free gadolinium was equal to zero, and the concentration of excess free DOTA was adjusted to a value of between 200 and 1500 ppm, relative to the complex. The reaction batch was made up to a total volume of 200 ml and filtered.

EXAMPLE 3

13.5 g of DOTA was suspended in 150 ml of water at a temperature of 75° C. 5.9 g of gadolinium oxide was added, and the batch was stirred at 75° C. for 30 minutes. In addition, 13.5 g of DOTA and 5.9 g of gadolinium oxide were added and stirred at 75° C. for 30 minutes. Once again, 13.5 g of DOTA and 6.0 g of gadolinium oxide were added and stirred at 75° C. for 30 minutes. The solution that was produced was mixed with 19.5 g of meglumine and stirred at 75° C. for one hour. Then, the content of free DOTA, free gadolinium, and complex was determined, and the final content of excess free DOTA was set. The concentration of free gadolinium was to be equal to zero, and the concentration of excess free DOTA was adjusted to a value of between 200 and 1500 ppm, relative to the complex. The reaction batch was made up to a total volume of 200 ml and filtered.

As shown in the examples, with the method according to the invention, the final content of excess DOTA can be set to 200-1500 ppm.

When the method according to the invention is carried out, the content of free gadolinium is always zero, since the procedure is performed with an excess of DOTA. When the method according to the invention is carried out, gadolinium is added in order to adjust the proportion of DOTA to the above-mentioned range.

When the method according to the invention is carried out, the substances gadolinium and DOTA can be added alternately. For example, one-third each of the target quantity is added at half-hour intervals.

At the beginning of the method according to the invention, gadolinium can be introduced. Then, a portion, e.g., one-fourth of the target quantity, of DOTA, is added.

The thus obtained solution is stirred, for example, at 80° C., e.g., for 2 hours, and then the remaining amount of DOTA is added to the solution.

In summary, an embodiment of the invention can be described as follows:

A method for producing a liquid pharmaceutical preparation, which contains a complex that consists of gadolinium and DOTA as well as a base such as L-lysine or meglumine, comprises, for example, the following steps:

a) An aqueous solution, consisting of DOTA, gadolinium, and a base such as meglumine or L-lysine, is produced.
b) The content of free DOTA and free gadolinium in the solution that is obtained according to step a) is determined.
c) Free gadolinium and/or free DOTA is/are added in order to adjust the content of free DOTA to 200-1500 ppm, relative to the complex.
d) The complexing can be carried out at elevated temperature.
e) To set the final pH, another base is added.
f) The final volume of the preparation is set.

The invention claimed is:

1. A method for producing a liquid pharmaceutical preparation that contains a complex that consists of DOTA and gadolinium as well as a base the method comprising the following steps:
   a) producing an aqueous solution that consists of DOTA, gadolinium, and a base,
   b) determining the content of free DOTA and free gadolinium in the solution obtained according to step a),
   c) adding free gadolinium and/or free DOTA in order to adjust a content of free DOTA of 200-1500 ppm in the solution that is obtained according to step a), relative to the complex, whereby the addition of free DOTA and free gadolinium is carried out in such a way that there is no free gadolinium in the preparation,
   d) carrying out complexing at elevated temperature,
   e) adding more of the base in order to adjust the pH, and
   f) setting the final volume.

2. The method according to claim 1, wherein for producing the solution according to step a), first DOTA is dissolved in water at elevated temperature, and then gadolinium is added.

3. The method according to claim 1, wherein the complexing is completed by further addition of the base.

4. The method according to claim 1, wherein step a) is carried out at a temperature of between 60° C. and 95° C.

5. The method according to claim 1, wherein the solution is stirred when steps a) and/or d) is/are carried out.

6. The method according to claim 1, wherein in step c), the addition of free gadolinium and/or free DOTA is carried out in two or more than two partial amounts.

7. The method according to claim 1, wherein free DOTA is added in the form of a solution and/or free gadolinium is added in the form of a solution.

8. The method according to claim 1, wherein the gadolinium is added as an oxide ($Gd_2O_3$) and in the oxidation stage +III.

9. The method according to claim 1, wherein the concentration of free DOTA in the preparation is 180-2000 ppm relative to the complex.

10. The method according to claim 1, wherein the concentration of free gadolinium in the preparation is less than 10 ppm.

11. The method according to claim 1, wherein the pH in step e) is adjusted to a value of between 7.0 and 7.2.

12. The method of claim 1, wherein the base is meglumine or L-lysine.

13. The method of claim 3, wherein the base added is meglumine or L-lysine.

14. The method according to claim 2, wherein the complexing is completed by further addition of the base.

15. The method according to claim 2, wherein step a) is carried out at a temperature of between 60° C. and 95° C.

16. The method according to claim 3, wherein step a) is carried out at a temperature of between 60° C. and 95° C.

17. The method according to claim 2, wherein the solution is stirred when steps a) and/or d) is/are carried out.

18. The method according to claim 3, wherein the solution is stirred when steps a) and/or d) is/are carried out.

19. The method according to claim 4, wherein the solution is stirred when steps a) and/or d) is/are carried out.

20. The method according to claim 2, wherein in step c), the addition of free gadolinium and/or free DOTA is carried out in two or more than two partial amounts.

* * * * *